United States Patent
Magno et al.

(10) Patent No.: US 11,576,683 B2
(45) Date of Patent: Feb. 14, 2023

(54) ROTATABLE SURGICAL INSTRUMENT WITH BEARING

(71) Applicant: GYRUS ACMI, INC., Southborough, MA (US)

(72) Inventors: Joey Magno, Cordova, TN (US); Canh S. Ly, Cordova, TN (US); Reid M. Anderson, Lakeland, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 17/031,389

(22) Filed: Sep. 24, 2020

(65) Prior Publication Data

US 2021/0100564 A1    Apr. 8, 2021

Related U.S. Application Data

(60) Provisional application No. 62/979,773, filed on Feb. 21, 2020, provisional application No. 62/910,598, filed on Oct. 4, 2019.

(51) Int. Cl.
*A61B 17/16*    (2006.01)

(52) U.S. Cl.
CPC ...... *A61B 17/1615* (2013.01); *A61B 17/1624* (2013.01); *A61B 2217/005* (2013.01)

(58) Field of Classification Search
CPC ............ A61B 17/1615; A61B 17/1617; A61B 17/162; A61B 17/1622; A61B 17/1626; A61B 17/1628; A61B 17/1631; A61B 17/1633; A61B 17/1635; A61B 17/1637; A61B 17/164; A61B 17/1642;

(Continued)

(56) References Cited

U.S. PATENT DOCUMENTS 5,383,884 A * 1/1995 Summers ......... A61B 17/32002
606/170
9,155,555 B2    10/2015 Obrien
(Continued)

FOREIGN PATENT DOCUMENTS

| EP | 1702573 A1 | 9/2006 |
|---|---|---|
| WO | WO-0122890 A1 | 4/2001 |
| WO | WO-2019049736 A1 | 3/2019 |

OTHER PUBLICATIONS

"European Application Serial No. 20199555.2, Extended European Search Report dated Feb. 22, 2021", 8 pgs.

(Continued)

*Primary Examiner* — Matthew J Lawson
(74) *Attorney, Agent, or Firm* — Schwegman Lundberg & Woessner, P.A.

(57) ABSTRACT

A rotatable surgical instrument, system, and method includes an outer tubular member and an inner tubular member contained, at least in part, within the outer tubular member and configured to rotate relative to the outer tubular member. A distal tip is coupled to and configured to rotate with the inner tubular member, the distal tip forming a channel around a portion of the distal tip. A bearing is rotatably positioned within the channel, wherein the channel inhibits radial and axial movement of the bearing, with respect to the distal tip, along a major axis of the outer tubular member and inner tubular member, and wherein the bearing is configured to inhibit deflection of the distal tip from the major axis.

11 Claims, 6 Drawing Sheets

(58) Field of Classification Search
CPC ............ A61B 17/1644; A61B 17/1655; A61B 17/1657; A61B 17/1659
See application file for complete search history.

(56) References Cited

U.S. PATENT DOCUMENTS

| | | | |
|---|---|---|---|
| 10,321,919 B2 | 6/2019 | Dougherty et al. | |
| 2002/0151902 A1* | 10/2002 | Riedel .................. | A61B 17/162 606/80 |
| 2012/0259337 A1* | 10/2012 | del Rio .............. | A61B 17/1617 606/80 |
| 2013/0197552 A1 | 8/2013 | Obrien, II | |
| 2017/0100136 A1* | 4/2017 | Dougherty ......... | A61B 17/1633 |

OTHER PUBLICATIONS

"European Application Serial No. 20199555.2, Response Filed Oct. 6, 2021 to Extended European Search Report dated Feb. 22, 2021", 10 pgs.

\* cited by examiner

ROTATABLE SURGICAL INSTRUMENT WITH BEARING

CROSS-REFERENCE TO RELATED APPLICATIONS

This application claims the benefit of U.S. Provisional Patent Application Ser. No. 62/910,598, filed on Oct. 4, 2019 and U.S. Provisional Patent Application Ser. No. 62/979,773, filed on Feb. 21, 2020, the contents of which are incorporated herein in their entireties.

TECHNICAL FIELD

The subject matter disclosed herein generally relates to a rotatable surgical instrument with a bearing to facilitate rotation and inhibit radial and axial movement of the distal tip.

BACKGROUND

Rotatable surgical instruments have been utilized to perform surgical operations such as drilling, cutting, and the like. Such surgical instruments have included an elongate tubular member with a burr fixed to the end. The burr is induced to rotate at high speed to cut through material, up to and including bone and other hard materials.

BRIEF DESCRIPTION OF THE DRAWINGS

Some embodiments are illustrated by way of example and not limitation in the figures of the accompanying drawings.

DETAILED DESCRIPTION

Example methods and systems are directed to a rotatable surgical instrument with a bearing to facilitate rotation and inhibit radial and axial movement of the distal tip. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Because such surgical instrument may rotate at very high speeds, an outer tubular member or sheath may be utilized to isolate certain rotatable portions from external interference, thereby protecting the surgical instrument as well as users of the rotatable instrument. However, the outer tubular member may interfere with the inner tubular member to which the burr or other distal tip is attached. As such, a bearing may be utilized to maintain separation between the inner tubular member and distal tip and the outer tubular member. However, the high rotational speeds may impart significant forces on the bearing and, if the bearing is not properly secured and positioned with respect to the distal tip and inner tubular member, may shift radially or axially with respect to the distal tip and inner tubular member. That may unbalance the rotatable instrument and/or cause undesired friction.

A rotatable surgical instrument has been developed that incorporates a bearing positioned within a channel that inhibits the radial and axial movement of the bearing with respect to the distal tip and inner tubular member. The bearing thereby protects the distal tip from friction with the outer tubular member while also reducing the likelihood of the bearing to introduce undesired friction or balance complications with the surgical instrument. The bearing may be a bushing, ball bearing, or any other suitable bearing.

Figure 1:
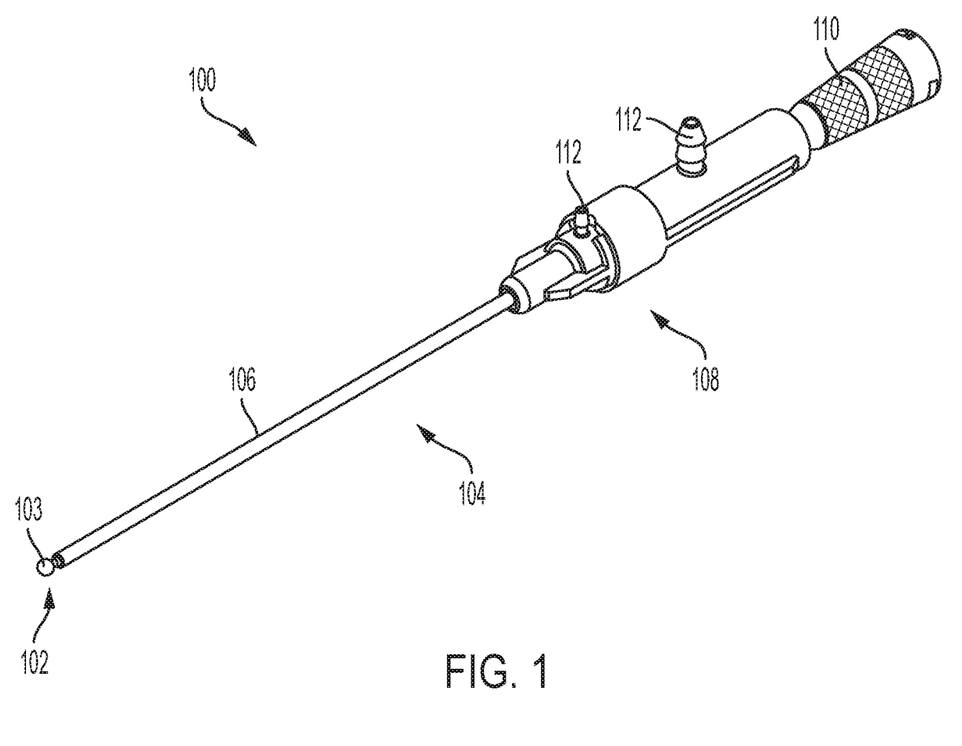
FIG. 1 is an image of a rotatable surgical instrument, in an example embodiment.
Figure 2A:
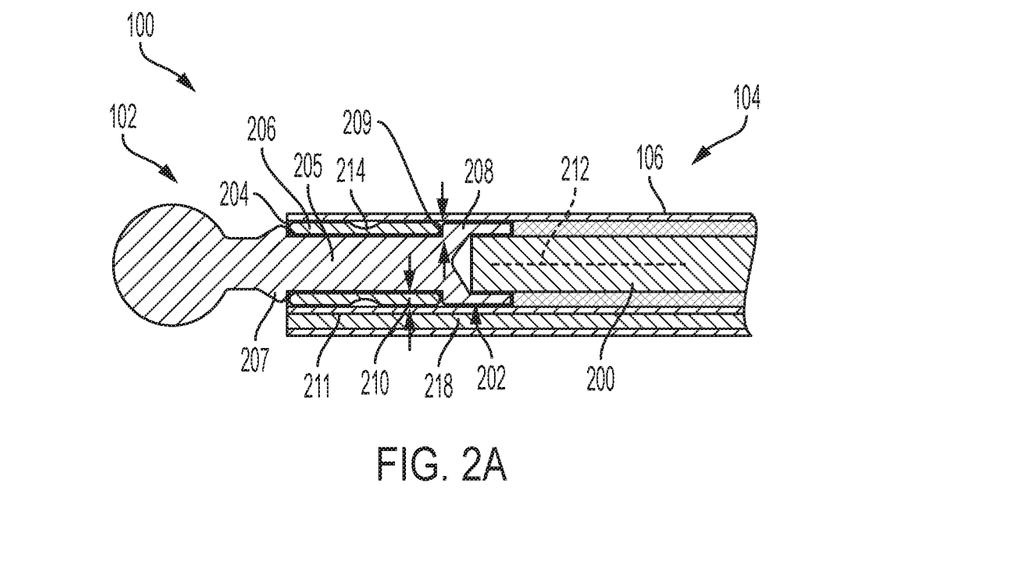
FIGS. 2A and 2B are, respectively, side and perspective cut-away detailed illustrations of a portion of the rotatable surgical instrument, in an example embodiment.

FIG. 1 is an image of a rotatable surgical instrument 100, in an example embodiment. The rotatable surgical instrument 100 includes a distal tip 102. In the illustrated example, the distal tip 102 includes a burr 103. In various alternative examples, the distal tip 102 is itself a burr or is or includes an alternative surgical device that is configured to rotate. An elongate portion 104 of the rotatable surgical instrument 100 includes a visible outer tubular member 106, such as a sheath, which contains at least in part therein an inner tubular member (not shown, see FIG. 2) that is directly coupled to the distal tip 102. The elongate portion 104 may be flexible or may be substantially rigid, depending on the uses for which the rotatable surgical instrument 100 is to be used.

In various examples, the outer tubular member 106 may be formed from stainless steel or any biocompatible material that is sufficiently resilient against the forces involved to safely contain various components disclosed herein. The outer tubular member 106 may be flexible, e.g., by including cuts in the outer tubular member 106 to enable to the outer tubular member 106 to be bent or otherwise flex. In such examples, certain components contained therein may also be flexible. In various examples, the distal tip 102 may also be stainless steel or any other biocompatible material that is sufficiently resilient to enable the distal tip 102 to cut, grind, or otherwise engage with the targeted material.

The rotatable surgical instrument 100 may include or may be attached to an adapter 108 and a motor housing 110. The motor housing 110 is an attachment or adapter that is part of a handpiece where a motor resides. The motor causes the distal tip 102 to rotate at a desired rate while not inducing rotational force on the outer tubular member 106. In the illustrated example, the adapter 108 includes ports 112 for applying suction to facilitate removal of debris and/or irrigation of the distal tip 102 to facilitate operation of the rotatable surgical instrument 100, as disclosed in detail herein.

Figure 2B:
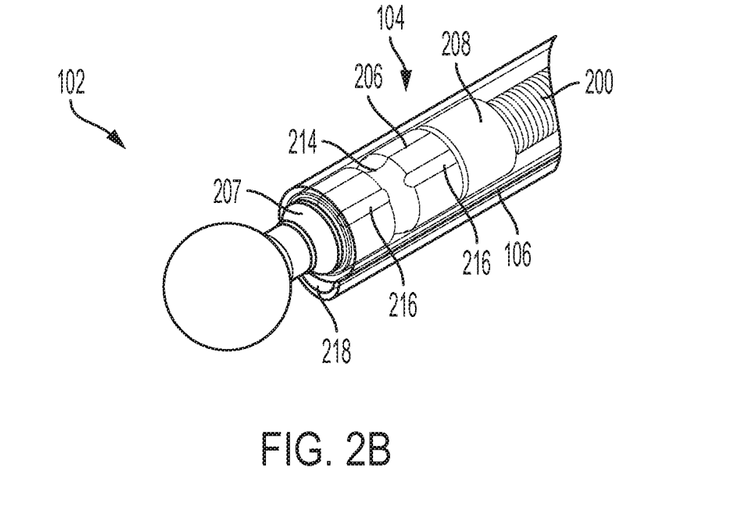

FIGS. 2A and 2B are, respectively, side and perspective cut-away detailed illustrations of a portion of the rotatable surgical instrument 100, in an example embodiment. The elongate portion 104 further includes the inner tubular member 200 positioned within the outer tubular member 106. The inner tubular member 200 is coupled to a proximal end 202 of the distal tip 102. The inner tubular member 200 is coupled or coupleable to the motor. When the motor imparts rotational force on the inner tubular member 200 the inner tubular member 200 and the distal tip 102 may rotate together with respect to the outer tubular member 106. In various examples, the motor is configured to rotate the inner tubular member 200 and distal tip 102 at thousands or tens of thousands of revolutions per minute. In various examples, the inner tubular member 200 is made of metal formed into, e.g., a coiled flat wire or a clockwise and/or counterclockwise coiled wire.

The distal tip 102 forms a channel 204 around a portion 205 of the distal tip 102. A bearing 206 is rotatably seated in the channel 204. In the illustrated example, the channel 204 is formed by a midsection flange 207 and a collar 208 at the proximal end 202, though it is to be recognized that any suitable configuration of the distal tip 102 that forms a channel to contain the bearing 206 may be utilized. The collar 208 is configured to admit an end of the inner tubular member 200 and secure the distal tip 102 to the inner tubular member 200. As such, the collar 208 represents a female connector configured to secure a male connector, such as a stud, of the inner tubular member 200.

The channel 204 has a depth 209 from a top of the midsection flange 207 and/or collar 208, whichever is higher. The depth 209 is less than a thickness 210 of the bearing 206 to allow the bearing 206 to contact both the distal tip 102 and an inner surface 211 of the outer tubular member 106. The channel 204 allows the bearing 206 to rotate with respect to the distal tip 102 and vice versa while inhibiting the bearing 206 from moving radially and axially along a major axis 212 of the outer tubular member 106, inner tubular member 200, and distal tip 102 outside of the channel 204. For the purposes of this application, rotation of the distal tip 102 is to be understood as rotating about the major axis 212.

In the illustrated example, the bearing 206 is a bushing. The bearing 206 includes an indentation 214 to enable the outer tubular member 106 to be crimped partially into the indentation 214 to further secure the bearing 206 with respect to the outer tubular member 106. In such an example, the bearing 206 may not rotate with respect to the outer tubular member 106 or may otherwise have rotation with respect to the outer tubular member 106 inhibited, e.g., by rotating at a rate less than the rotation of the distal tip 102, in various examples only a few percentage points as much as the rate of the distal tip 102. The bearing 206 further forms suction pathways 216 which are in fluid communication between the distal tip 102 and a port 112 that may be coupled to a vacuum source. The induced suction may draw particulates from the distal tip, through the suction pathways 216, and down gaps between the inner tubular member 200 and outer tubular member 106 to the port 112. In various examples, the bearing 206 is comprised of or formed from stainless steel, ceramic, bronze, beryllium copper, or any suitable material.

As illustrated, the outer tubular member 106 includes or is coupled to an external irrigation channel 218. The irrigation channel 218 is in fluid communication with a port 112 which may be coupled to a source of irrigation fluid. The irrigation channel 218 may deliver irrigation fluid onto and in proximity of the distal tip 102 to decrease heating of and wear on the distal tip 102, e.g., when the distal tip 102 is or includes a burr. In various examples, the irrigation channel 218 may be omitted.

The positioning of bearing 206 within the channel 204 and the addition of the crimp into the indentation 214 generally maintains the distal tip 102 in a consistent position with respect to the outer tubular member 106 while the distal tip 102 is rotating. The distal tip 102 is generally inhibited from moving radially and axially along the major axis 212 of rotatable medical instrument as well as deflecting from or "wobbling" about the major axis 212. In an example embodiment, for a distal tip 102 having a diameter of approximately four (4) millimeters, a maximum axial movement along and/or deflection from the major axis 212 may be from approximately 0.1016 to 0.2032 millimeters (approximately 0.004 to 0.008 inches). As such, the rotatable medical instrument 100 may be relatively more stable and precise in use while also reducing wear and tear on the rotatable medical instrument 100 and on the motor and other ancillary equipment.

Figure 3:
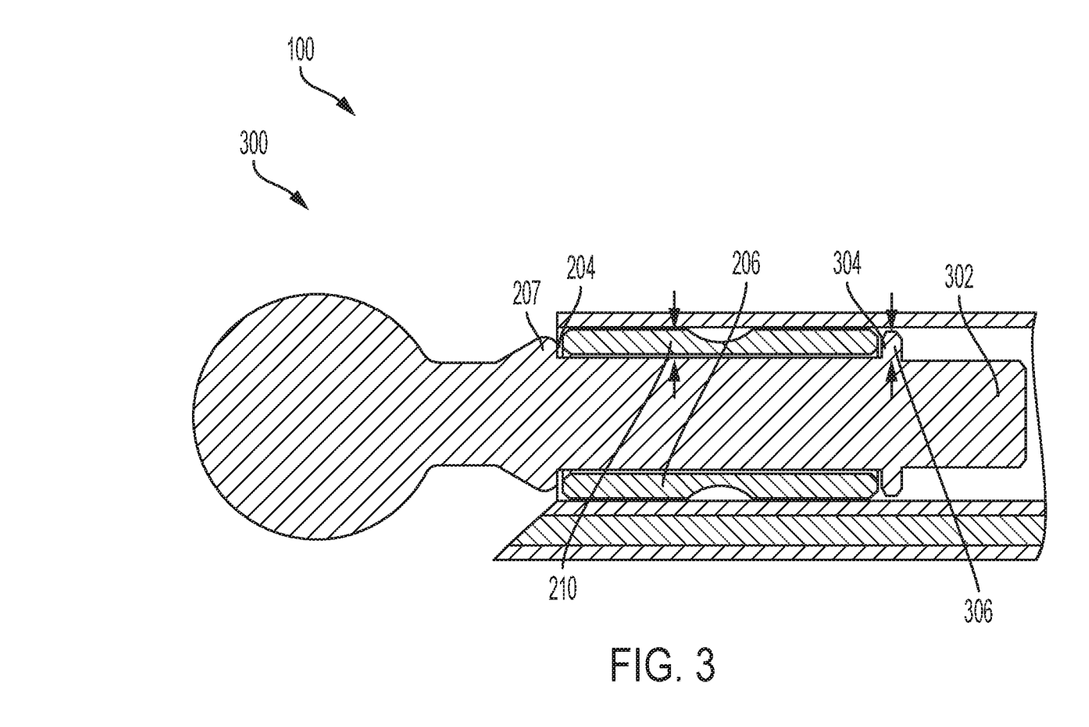
FIG. 3 is a perspective view detail view of the rotatable surgical instrument with an alternative distal tip, in an example embodiment.

FIG. 3 is a detail view of the rotatable surgical instrument 100 with an alternative distal tip 300, in an example embodiment. In contrast to the collar 208 of the distal tip 102 illustrated in FIG. 2, the distal tip 300 includes male connector or stud 302 to receive a female connector (not depicted) of the inner tubular member 200 to secure the distal tip 300 to the inner tubular member 200. The stud 302 may be solid or otherwise configured to form a robust connection with the inner tubular member 200.

While the alternative distal tip 300 is illustrated with the male connector 302, it is to be recognized and understood that the alternative distal tip 300 may instead incorporate a female connector as illustrated with respect to the collar 208 of the distal tip 102 and which is configured to connect with the male connector of the inner tubular member 200. Similarly, the distal tip 102 may instead incorporate the stud 302 and be configured to engage with a female connector on the inner tubular member 200. As such, it is to be recognized and understood that any male/female connector combination that is disclosed for one distal tip and inner tubular member combination herein may be utilized with respect to any of the other distal tip and inner tubular member combinations disclosed herein. It is further to be recognized and understood that while male/female connectors are disclosed specifically that any suitable connector combination may be implemented instead of the male/female connectors.

To form the channel 204, the distal tip 300 includes a proximal flange 304 in addition to the midsection flange 207. In the illustrated example, the proximal flange 304 has a height 306 greater than that of the midsection flange 207, making the depth of the channel 204 equal to that of the height of 306 of the proximal flange 304. As illustrated, however, the depth of the channel 204 nonetheless is less than that of the thickness 210 of the bearing 206.

Figure 4A:
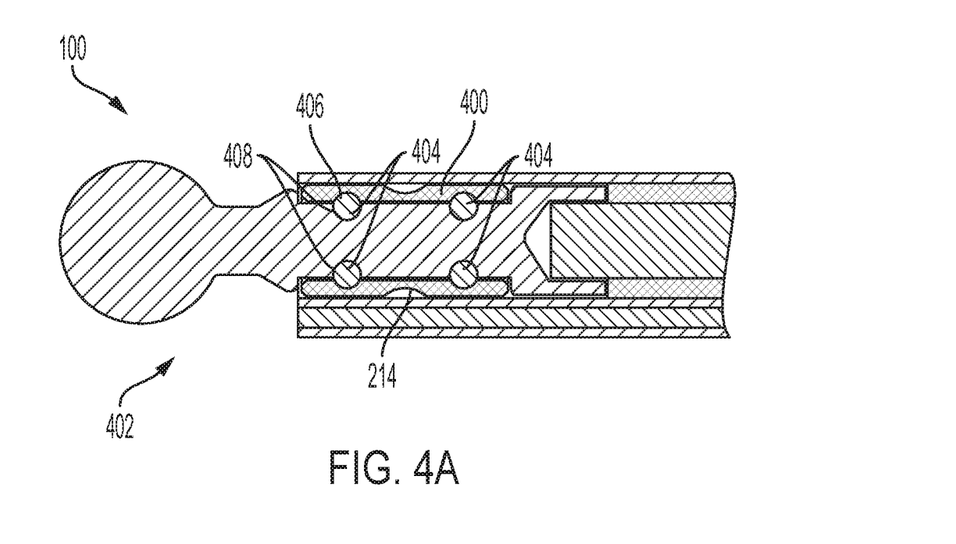
FIGS. 4A and 4B are side and cross-sectional illustrations of the rotatable surgical instrument having an alternative example of a bearing and distal tip, in an example embodiment.
Figure 4B:
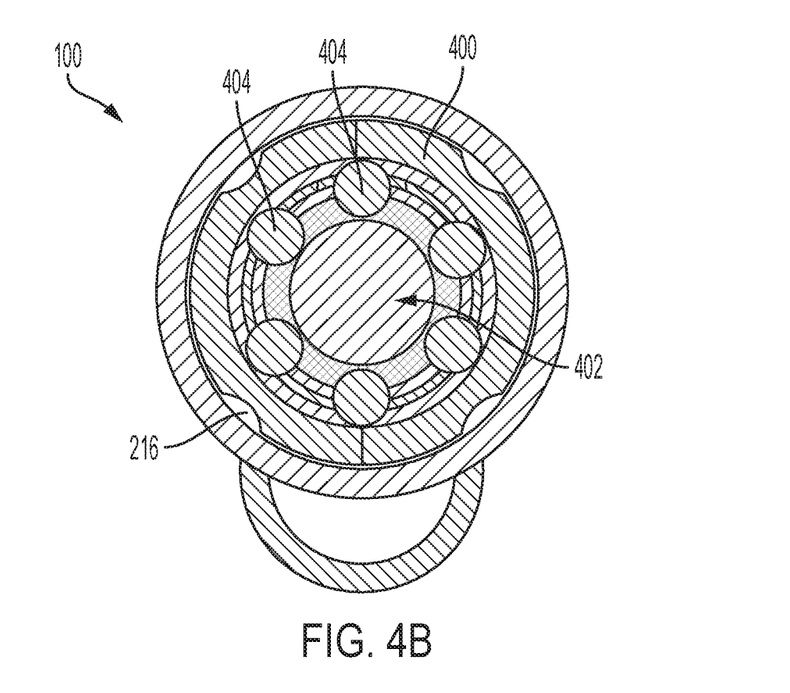

FIGS. 4A and 4B are side and cross-sectional illustrations, respectively, of the rotatable surgical instrument 100 having an alternative example of a bearing 400 and distal tip 402, in an example embodiment. The bearing 400 is a ball bearing including balls 404 positioned within bearing ball grooves 406 formed in the bearing 400 and facing the distal tip 402 and distal tip ball grooves 408 formed in the distal tip 402. The configuration of the bearing 400 is otherwise the same as that of the bearing 206, including the suction pathways 216 and indentations 214, while the configuration of the distal tip 402 is otherwise the same as the distal tip 102.

For the sake of illustration, six balls 404 are illustrated. However, it is to be recognized and understood that the number of balls 404 may be increased or decreased as desired. In an example, the number of balls 404 is selected, and the balls 404 are sized, to enable as many balls 404 to be placed in each ball groove 406 as possible while still allowing some or all of the balls 404 to maintain contact with the bearing 400 and the distal tip 402.

Figure 5:
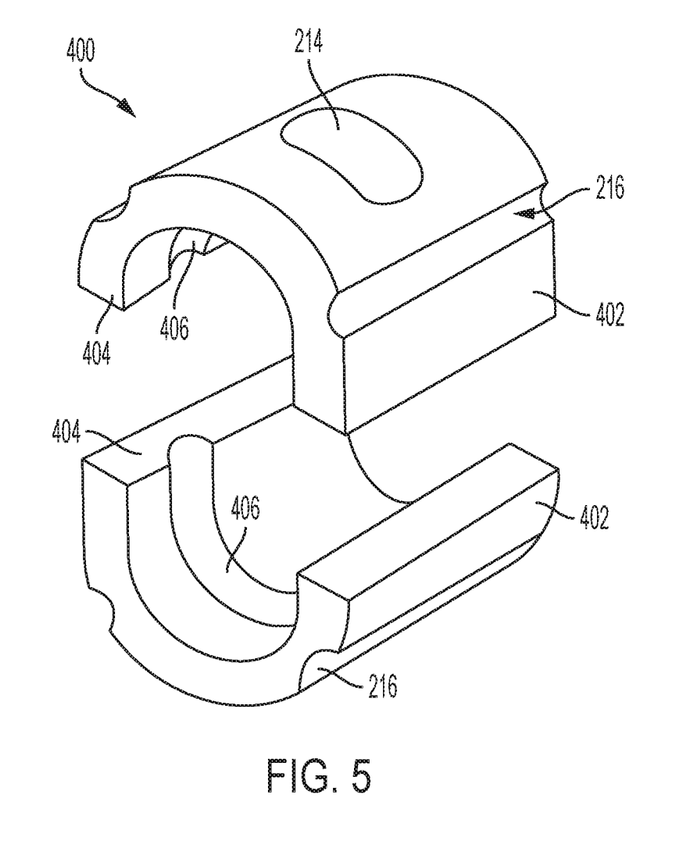
FIG. 5 is a perspective, exploded depiction the bearing, in an example embodiment.

FIG. 5 is a perspective, exploded depiction the bearing 400, in an example embodiment. In the illustrated example, the bearing 400 is formed from two segments 402, each forming a semicircular arc and which are otherwise the identical to one another and may be cast or molded from the same source. In the illustrated example, the segments 402 are configured to be welded or otherwise secured to one another along their longitudinal edges 404. In alternative examples, the segments 402 are not configured to be secured to one another and are instead maintained in relation to one another in the channel 204. In a further alternative example, the segments 402 are configured to snap together or otherwise secured to one another through a mechanical mechanism. As illustrated with respect to FIGS. 4A and 4B, the bearing 400 includes the ball grooves 406, indentation 214, suction pathways 216.

Forming the bearing 400 from two segments 402 may provide for efficiencies in manufacturing, but it is to be recognized and understood that the bearing 400 may be formed from any suitable mechanism or manufacturing process and may include more or fewer segments, including being formed from a single piece. In various examples, the bearing 400 may be formed through 3D printing within the channel 204. The principles described with respect to making or otherwise manufacturing the bearing 400 may be applied to the bearing 206, to any other bearing disclosed herein, or any other bearing that may be utilized in the manner of the bearings disclosed herein.

Figure 6:
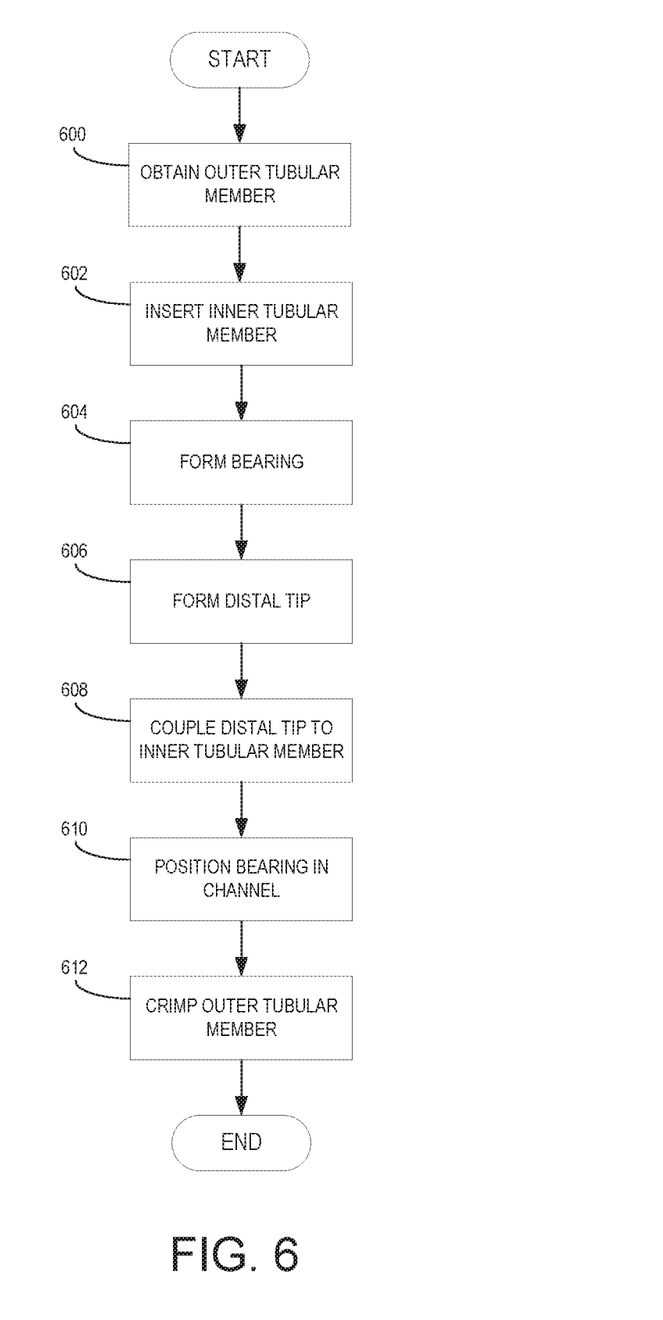
FIG. 6 is a flowchart for making the rotatable medical instrument, in an example embodiment.

FIG. 6 is a flowchart for making the rotatable medical instrument 100, in an example embodiment.

At 600, an outer tubular member is obtained.

At 602, an inner tubular member is inserted at least in part within the outer tubular member, the inner tubular member configured to rotate relative to the outer tubular member.

At 604, the bearing is formed. In an example, the bearing is a bushing. In an example, the bearing is a ball bearing comprising a bearing ball groove facing a distal tip and balls positioned in part within the ball groove and configured to be in contact with the portion of the distal tip. In an example, the bearing forms an outer channel proximate the outer tubular member.

At 606, the distal tip is formed. In an example, the channel has a depth less than a thickness of the bearing and wherein the bearing is configured to contact an inner surface of the outer tubular member. In an example, the distal tip forms a distal tip ball groove and wherein the balls are further positioned in part in the distal tip ball groove and in part in the bearing ball groove. In an example, the channel is formed by a midsection flange and a collar of the distal tip. In an example, the collar to admit an end of the inner tubular member and secure the distal tip to the inner tubular member. In an example, the channel is formed by a midsection flange and a proximal flange.

At 608, the distal tip is coupled to the inner tubular member, the distal tip forming a channel around a portion of the distal tip, the distal tip configured to rotate with the inner tubular member.

At 610, the bearing is positioned within the channel, the bearing being rotatable, wherein the channel inhibits radial and axial movement of the bearing, with respect to the distal tip, along a major axis of the outer tubular member and inner tubular member, and wherein the bearing is configured to inhibit deflection of the distal tip from the major axis.

At 612, the outer tubular member is crimped proximate the outer channel to inhibit radial and axial movement of the bearing and distal tip with respect to the outer tubular member and inhibit rotation of the bearing with respect to the outer tubular member.

ADDITIONAL NOTES

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The disclosure, therefore, is not to be taken in a limiting sense, and the scope of various embodiments includes the full range of equivalents to which the disclosed subject matter is entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. An Abstract, if provided, is included to comply with United States rule 37 C.F.R. § 1.72(b), to allow the reader to quickly ascertain the nature of the technical disclosure. It is submitted with the understanding that it will not be used to interpret or limit the scope or meaning of the claims. Also, in the above Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A rotatable surgical instrument, comprising:
an outer tubular member;
an inner tubular member contained, at least in part, within the outer tubular member and configured to rotate relative to the outer tubular member;
a distal tip coupled to and configured to rotate with the inner tubular member, the distal tip forming a channel around a portion of the distal tip; and
a bearing rotatably positioned within the channel, wherein the channel inhibits radial and axial movement of the bearing, with respect to the distal tip, along a major axis of the outer tubular member and inner tubular member, and wherein the bearing is configured to inhibit deflection of the distal tip from the major axis;
wherein the bearing has a suction pathway in fluid communication with the distal tip and a gap between the inner tubular member and the outer tubular member, the suction pathway configured to draw particulates from the distal tip when suction is applied to the suction pathway, the suction pathway further configured to inhibit axial movement of the bearing in conjunction with the inner tubular member and the outer tubular member.

2. The rotatable surgical instrument of claim 1, wherein the channel has a depth less than a thickness of the bearing and wherein the beating is configured to contact an inner surface of the outer tubular member.

3. The rotatable surgical instrument of claim 2, wherein the bearing is a bushing.

4. The rotatable surgical instrument of claim 2, wherein the bearing is a ball bearing comprising a bearing ball groove facing the distal tip and balls positioned in part within the ball groove and configured to be in contact with the portion of the distal tip.

5. The rotatable surgical instrument of claim 4, wherein the distal tip forms a distal tip ball groove and wherein the balls are further positioned in part in the distal tip ball groove and in part in the bearing ball groove.

6. The rotatable surgical instrument of claim 2, wherein the bearing forms an outer channel proximate the outer tubular member and wherein the outer tubular member is crimped proximate the outer channel to inhibit the radial and axial movement of the bearing and distal tip with respect to the outer tubular member and inhibit rotation of the bearing with respect to the outer tubular member.

7. The rotatable surgical instrument of claim 2, wherein the channel is formed by a midsection flange and a collar of the distal tip.

8. The rotatable surgical instrument of claim 7, wherein the collar is configured to admit an end of the inner tubular member and secure the distal tip to the inner tubular member.

9. The rotatable surgical instrument of claim 2, wherein the channel is formed by a midsection flange and a proximal flange.

10. The rotatable surgical instrument of claim 1, further comprising a port in fluid communication with the suction pathway, the port configured to be coupled to a vacuum source to apply suction to the suction pathway.

11. The rotatable surgical instrument of claim 1, wherein the distal tip has a burr on a distal side of the distal tip relative to the portion, and the beating is disposed between the outer tubular member and the distal side of the portion.

* * * * *

UNITED STATES PATENT AND TRADEMARK OFFICE
CERTIFICATE OF CORRECTION

PATENT NO. : 11,576,683 B2
APPLICATION NO. : 17/031389
DATED : February 14, 2023
INVENTOR(S) : Magno et al.

Page 1 of 1

It is certified that error appears in the above-identified patent and that said Letters Patent is hereby corrected as shown below:

In the Claims

In Column 8, Line 28, in Claim 2, delete "beating" and insert --bearing-- therefor In Column 8, Line 65, in Claim 11, delete "beating" and insert --bearing-- therefor Signed and Sealed this
Twenty-third Day of July, 2024

Katherine Kelly Vidal
*Director of the United States Patent and Trademark Office*